(12) United States Patent
Leierer

(10) Patent No.: US 8,980,238 B2
(45) Date of Patent: Mar. 17, 2015

(54) MUCOADHESIVE POLYMERS HAVING VITAMIN B PARTIAL STRUCTURES

(75) Inventor: Johannes Leierer, Innsbruck (AT)

(73) Assignees: Thiomatrix Forschungs—Und Beratungs GmbH, Innsbruck (AT); Croma Pharma GmbH, Leobendorf (AT)

( * ) Notice: Subject to any disclaimer, the term of this patent is extended or adjusted under 35 U.S.C. 154(b) by 0 days.

(21) Appl. No.: 13/499,099

(22) PCT Filed: Sep. 29, 2010

(86) PCT No.: PCT/EP2010/064464
§ 371 (c)(1),
(2), (4) Date: Mar. 29, 2012

(87) PCT Pub. No.: WO2011/039259
PCT Pub. Date: Apr. 7, 2011

(65) Prior Publication Data
US 2012/0225024 A1    Sep. 6, 2012

(30) Foreign Application Priority Data

Sep. 30, 2009  (AT) .................................. 1540/2009

(51) Int. Cl.
*A61K 47/36* (2006.01)
*A61K 8/73* (2006.01)
(Continued)

(52) U.S. Cl.
CPC ......... *A61K 47/48176* (2013.01); *A61K 9/0043* (2013.01); *A61K 9/006* (2013.01);
(Continued)

(58) Field of Classification Search
CPC ....... A61K 9/0043; A61K 9/006; A61K 9/06; A61K 9/2027; A61K 9/2031; A61K 9/205; A61K 47/4823; A61K 47/32; A61K 47/34; A61K 47/36; A61K 47/38
See application file for complete search history.

(56) References Cited

U.S. PATENT DOCUMENTS 4,521,425 A * 6/1985 Grassetti ...................... 514/350
5,763,579 A   6/1998 Gagnieu et al.
7,354,600 B1 * 4/2008 Bernkop-Schnurch ....... 424/486

FOREIGN PATENT DOCUMENTS

CS    200754      9/1980
EP    0305749 A1  3/1989
(Continued)

OTHER PUBLICATIONS

Millotti G., Samberger, C., Fröhlich, E., and Bernkop-Schnürch, A. "Chitosan-graft-6-mercaptonicotinic Acid: Synthesis, Characterization, and Biocompatability". Biomacromolecules. Epub Oct. 12, 2009. 10:3023-3027.*

(Continued)

*Primary Examiner* — Ileana Popa
*Assistant Examiner* — Nicole Babson
(74) *Attorney, Agent, or Firm* — Lando & Anastasi, LLP

(57) ABSTRACT

Because of the formation of disulfide bridges with mucus glycoproteins, the mucoadhesive properties of polymeric compounds can be significantly improved by the covalent attachment of thiol substructures to them. By the transformation of free thiol groups on such polymers in disulfides with mercaptonicotinamides or mercaptopyridoxins these thiol groups become comparatively more reactive resulting in significantly improved mucoadhesive properties. Furthermore, polymers exhibiting disulfide partial structures with mercaptonicotinamides or mercaptopyridoxins do not need to be protected against oxidation. In addition, they show comparatively higher permeation enhancing properties.

8 Claims, 3 Drawing Sheets

(51) Int. Cl.
  *A61K 47/32* (2006.01)
  *A61Q 5/06* (2006.01)
  *C08B 37/06* (2006.01)
  *C09D 133/02* (2006.01)
  *C08F 8/34* (2006.01)
  *C09J 133/02* (2006.01)
  *C08B 37/08* (2006.01)
  *A61K 47/48* (2006.01)
  *A61K 9/00* (2006.01)
  *A61K 9/06* (2006.01)
  *A61K 9/20* (2006.01)
  *A61K 47/34* (2006.01)
  *A61K 47/38* (2006.01)

(52) U.S. Cl.
  CPC .............. *A61K 9/06* (2013.01); *A61K 9/2027* (2013.01); *A61K 9/2031* (2013.01); *A61K 9/205* (2013.01); *A61K 9/2054* (2013.01); *A61K 47/32* (2013.01); *A61K 47/34* (2013.01); *A61K 47/36* (2013.01); *A61K 47/38* (2013.01); *A61K 47/4823* (2013.01)
  USPC .................. 424/70.13; 536/20; 536/2; 536/3; 514/777; 514/772.1; 525/329.8; 524/556

(56) References Cited

FOREIGN PATENT DOCUMENTS

| | | |
|---|---|---|
| EP | 1126881 A1 | 8/2001 |
| WO | 9607676 A1 | 3/1996 |
| WO | 00/25823 A1 | 5/2000 |
| WO | 01/32623 A1 | 5/2001 |

OTHER PUBLICATIONS

International Report on Patentabliity for PCT/EP2010/064464 mailed Apr. 11, 2012.
International Search Report or PCT/EP2010/064464 mailed Aug. 18, 2011.
Leitner, et al., "Thiolated polymers: 1-10 evidence for the formation of disulphide bonds with mucus glycoproteins" European Journal of Pharmaceutics and Biopharmaceutics. Elsevier Science Publishers B. V. Amsterdam. NL. vol. 56. No. 2. Sep. 1, 2003. pp 207-214.
Written Opinion for PCT/EP2010/064464 mailed Apr. 4, 2012.
Akiyama et al., "Evaluation of oral mucoadhesive microspheres in man on the basis of the pharmacokinetics of furosemide and riboflavin, compounds with limited gastrointestinal absorption sites." J. Pharm. Pharmacol. 50 (1998) 159-166.
Bernkop-Schnurch et al., "Improvement in the mucoadhesive properties of alginate by the covalent attachment of cysteine." J. Control. Release, 71 (2001) 277-285.
Bernkop-Schnurch et al., "Thiolated polymers—thiomers: synthesis and in vitro evaluation of chitosan-2-iminothiolane conjugates." Int. J. Pharm., 260 (2003) 229-237.
Bernkop-Schnurch and Hopf Sci. Pharm., 69 (2001) 109-118.
Bernkop-Schnurch Sci. Pharm., Int. J. Pharm., 194, (2000) 239-247.
Blackwood et al. J. Am. Chern. Soc., 80 (1958) 6244-6249.
Hombach et al., "Development and in vitro evaluation of a mucoadhesive vaginal delivery system for nystatin." J Pharm Sci. 98 (2009) 555-564.
Kafedjiiski et al., "Improved synthesis and in vitro characterization of chitosan-thioethylamidine conjugate." Biomaterials, 27 (2006) 127-135.
Kafedjiiski et al., "Synthesis and in vitro evaluation of a novel chitosan-glutathione conjugate." Pharm Res., 22 (2005) 1480-1488.
Kafedjiiski et al., "Synthesis and in vitro evaluation of thiolated hyaluronic acid for mucoadhesive drug delivery." Int. J. Pharm., 343, (2007) 48-58.
Karami et al., "Urea- hydrogen peroxide (UHP) oxidation of thiols to the corresponding disulfides promoted by maleic anhydride as mediator." Molecules, 10 (2005) 1385-63.
Majzoob et al., J. Pharm. Pharmacol., 58 (2006) 1601-1610.
Perera et al., "Hydrophobic Thiolation of Pectin with 4-Aminothiophenol: Synthesis and in Vitro Characterization" AAPS PharmSciTech. , 11 (2010) 174-180.
Roldo et al., "Mucoadhesive thiolated chitosans as platforms for oral controlled drug delivery: synthesis and in vitro evaluation" Eur. J. Pharm. Biopharm., 57, 115-121.
Vetter et al., "Thiolated polycarbophil as an adjuvant for permeation enhancement in nasal delivery of antisense oligonucleotides." J Pharm Sci. 99 (2010) 1427-1439.
European Official Action dated Jun. 25, 2013 for Application No. 10 760 673.3 (with translation), 6 pages.
Foger et al., "Correlation of in vitro and in vivo models for the oral absorption of peptide drugs," Amino Acids, 35(1) (2008) 233-41.

\* cited by examiner

MUCOADHESIVE POLYMERS HAVING VITAMIN B PARTIAL STRUCTURES

CROSS-REFERENCE TO RELATED APPLICATION

This application is a national stage entry under 35 U.S.C. §371 of PCT application PCT/EP2010/064464, filed Sep. 29, 2010, which claims priority to Austrian Patent Application No. 1540/2009 filed Sep. 30, 2009.

DETAILED DESCRIPTION

Mucoadhesive polymers are polymeric compounds exhibiting comparatively high adhesive properties on mucosa. Mucoadhesive polymers are compounds such as (crosslinked) poly(meth)acrylates, (trimethylated) chitosans, hyaluronic acid, alginates, pectins and cellulose derivatives. The crosslinking of poly(meth)acrylates is achieved during polymerization by the addition of compounds exhibiting at least two vinyl_substructures such as di-vinylglycol or pentaerythritol allyl ether. Cellulose derivatives displaying mucoadhesive properties are over all sodium carboxymethylcellulose, hydroxyethylcellulose, ethylcellulose, methylcellulose and hydroxypropylmethylcellulose. Because of the improved adhesion of drug delivery systems on mucosa such as the small intestinal mucosa being responsible for drug uptake, drugs are comparatively more efficiently and more sustainably taken up in the systemic circulation. Evidence for this great advantage of mucoadhesive polymers in comparison to state-of-the-art drug delivery systems has already been provided in various studies [e.g. Akiyama et al., J. Pharm. Pharmacol. 50 (1998) 159-166].

By the covalent attachment of thiol partial structures to such polymers their mucoadhesive properties can be substantially improved, as these thiol groups are capable of forming covalent bonds via disulfide bridges with thiol partial structures of the mucus [Muco-adhesive polymers, use thereof and method for producing the same. EP 1126881]. Polymers with thiol partial structures—designated thiomers (thiolated polymers)—exhibit more than 100-fold improved adhesive properties on various mucosal membranes [e.g. Roldo et al., Eur. J. Pharm. Biopharm., 57, 115-121].

Despite thiolation, the mucoadhesive properties of polymers, however, are often insufficient in order to achieve the desired effect. The herein presented invention is therefore based on the object to overcome state-of-the-art problems described above and to provide mucoadhesive polymers exhibiting superior properties.

This object is fully solved by polymeric compounds, by the use of polymeric compounds, and by compositions of this invention. According to this invention vitamin B derivatives such as mercapto(iso)nicotinamides or mercaptopyridoxines are coupled to free thiol groups of thiomers via disulfide bridges as illustrated in FIG. 1 for 6-mercaptonicotinamides. Because of the coupling of these partial structures to thiomers they react substantially more rapidly and to a comparatively higher degree with thiol groups of mucus glycoproteins and free thiol groups of thiomers, respectively. Apart from mercapto(iso)nicotinamides and mercaptopyridoxins, mercaptonicotinic acids are also suitable for this purpose. As they are responsible for numerous adverse effects such as vasodilatation or alterations of fat metabolism, however, mercaptonicotinamides and mercaptopyridoxines—i.e. vitamin B3- and vitamin B6-derivatives—are preferred according to this invention. As starting polymers according to the present invention are especially suitable: thiolated (crosslinked)poly (meth)acrylates such as polyacrylic acid-cysteamine conjugates [Hombach et al., J Pharm Sci. 98 (2009) 555-564] or polycarbophil-cysteine conjugates [Vetter et al., J Pharm Sci. 99 (2010) 1427-1439], thiolated chitosans such as chitosan-thioglycolic acid conjugates [Bernkop-Schnurch and Hopf Sci. Pharm., 69 (2001) 109-118], chitosan-mercaptonicotinic acid conjugates [Millotti et al., Biomacromolecules, 10 (2009) 3023-3027] or chitosan-glutathione conjugates [Kafedjiiski et al., Pharm Res., 22 (2005) 1480-1488], thiolated pectins such as pectin-cysteine conjugates [Majzoob et al., J. Pharm. Pharmacol., 58 (2006) 1601-1610] or pectin-4-mercaptoaminophenol conjugate [Perera et al., AAPS PharmSciTech., 11 (2010) 174-180], thiolated alginate such as alginate-cysteine conjugates [Bernkop-Schnurch et al., J. Control. Release, 71 (2001) 277-285], thiolated hyaluronic acid such as hyaluronic acid-cysteine ethyl ester conjugate [Kafedjiiski at al., Int. J. Pharm., 343, (2007) 48-58], thiolated polyallylamines such as polyallylamine-thioglycolic acid conjugates, thiolated polylysine, thiolated polyornithine, thiolated polyaminoamide, thiolated cellulose derivatives such as carboxymethylcellulose-cysteine conjugates [Bernkop-Schnurch, Int. J. Pharm., 194, (2000) 239-247], thiolated (crosslinked) polyvinylpyrrolidones, which are generated by the addition of S-protected thiol group bearing vinyl compounds such as S-acetyl-cysteine-acrylamide during the polymerisation of vinylpyrrolidone, as well as thiolated (crosslinked) (meth)acrylic acid/ethylacrylate co-polymers being prepared in analogy to thiolated polyvinylpyrrolidones. In addition, apart from the monomers allylamine, vinylpyrrolidone, (meth)acrylic acid and ethylacrylate also further monomers exhibiting a vinylsubstructure such as vinylalcohol, vinylimidazole, vinylcaprolactone or (meth)acrylamide can be polymerized with S-protected thiol group bearing vinyl compounds in any ratio. As thiol group bearing ligands are further suitable: mercaptobenzoic acid, N-acetyl-cysteine, homocysteine, 3-thio-proprionic acid, 4-thio-butanoic acid, thiobutylamidine as well as thioethylamidine [Kafedjiiski at al., Biomaterials, 27 (2006) 127-135]. Mediated by oxidation, mercaptonicotinamides and mercaptopyridoxines, respectively, are covalently attached to these mucoadhesive polymers forming disulfide bridges between the particular thiomer and free thiol group of the particular vitamin B derivative. According to a preferred embodiment of this invention a molar surplus of mercaptonicotinamide and mercaptopyridoxine, respectively, over the free thiol groups of the polymer are advantageous. By the addition of urea peroxide and maleic acid anhydride this oxidation process can be additionally accelerated as described by Kamari [Karami et al., Molecules, 10 (2005) 1385-63]. Furthermore, in a preferred embodiment the oxidation can be accelerated by the addition of hydrogen_peroxide. Generally, the oxidation process takes place more rapidly at higher pH-values. Polymers of this invention exhibit 10-1000 μmol of mercapto(iso)nicotinamide and mercaptopyridoxine partial structures and in particular 100-1000 μmol of mercapto(iso)nicotinamide and mercaptopyridoxine partial structures per gram polymer, respectively. The number of remaining thiol groups, which have not formed disulfide bridges with the ligand, can be controlled by the amount of each added vitamin B derivative.

According to this invention in particular 2-mercaptonicotinamide and 6-mercaptonicotinamide as well as 2- and 6-mercaptoisonicotinamide are useful mercaptonicotinamides. The synthesis of 6-mercaptonicotinamide is described in Example 1. The synthesis of further derivatives as mentioned above is performed in analogy. In particular 6-mercaptopyridoxine is according to this invention a suitable mercaptopyridoxine. Its synthesis is based on 6-chloropyridoxine, the synthesis of which is described by Blackwood et al. [Blackwood et al., J. Am. Chem. Soc., 80 (1958) 6244-6249]. The substitution of chlorine by a mercapto group is achieved according to the method described in Example 1.

Alternatively to this preparation method S-(2- or 6-mercapto(iso)nicotinamide- and S-(6-mercaptopyridoxine)-disulfides with vinyigroup(s) bearing compounds such as cysteine-acrylamide can be polymerized according to a preferred embodiment with other vinyl group(s) bearing monomers of choice such as (meth)acrylic acid, vinylpyrrolidone, vinylalcohol or ethylacrylate.

A further possibility for the synthesis of polymers of this invention is the covalent binding of S-(2- or 6-mercapto(iso) nicotinamide- or S-(6-mercaptopyridoxine)-disulfides with preactivated ligands to polymers. N-Succinimidyl 3-(2-nicotinamidyldithio)-proprionate, for instance, can be very efficiently coupled to polymers exhibiting primary amino groups (e.g. polyallylamine, chitosan) to form amide bindings.

A further advantage of compounds prepared in this way is that due to the transformation of free thiol groups to disulfides with mercaptonicotinamides and mercaptopyridoxines, respectively, they are not anymore sensitive to oxidation, as the thiol groups are already prevalent in the oxidized form. The combination of polymers of this invention with polymers exhibiting free thiol groups leads to the formation of disulfide bridges between these two polymers and consequently to a comparatively more rapid increase in viscosity. This effect can also be achieved when not all the thiol groups on the thiomer are transformed in disulfides with mercaptonicotinamides and mercaptopyridoxines, respectively.

Because of these mucoadhesive properties and the improved stability polymers of this invention are suitable for a broad range of applications in particular in the pharmaceutical and cosmetic field as well as in health-care products. Accordingly, the invention also provides the use of mucoadhesive polymers of this invention as pharmaceutical and cosmetic as well as health-care products. Furthermore, the invention provides a composition comprising one or several polymer(s) of this invention, drug(s), excipient(s) and/or solvent(s).

Apart from these improved mucoadhesive properties the permeation enhancing properties of thiomers are also improved by (iso)nicotinamide- and pyridoxine-disulfide side chains according to this invention. The apparent permeability coefficient (Papp) of fluorescence labeled dextran (molecular mass: 4.4 kDa; FD4) without polymer addition on freshly excised rat intestinal mucosa, for instance, was determined to be $9.6 \pm 3.5 \times 10^{-7}$ cm/s according to the method described by Foger et al. [Foger et al., Amino Acids, 35 (2008) 233-241], whereas it was 1.8-fold improved by the addition of 0.5% (m/v) chitosan-thioglycolic acid conjugate (molecular mass: 450 kDa; 234 .mu.mol thiol groups per gram polymer) and even 5.3-fold improved by the addition of 0.5% (m/v) of the same polymer at which entire free thiol groups were previously transformed to disulfides with 6-mercaptonicotinamide.

Polymers of this invention are useful in the pharmaceutical field as drug carrier matrix in tablets, as gelling excipients in semisolid and liquid formulations, as adhesive wound dressings, as scaffold in the field of tissue engineering as well as for the preparation of micro- and nanoparticulate drug delivery systems. In the cosmetic field are in particular, applications as hair care products such as hair styling gels, fixing agents, colorants, cleaning agents, and coatings for hair, lashes, eyebrows of interest, because of the protein structure of hair thiol-partial structures present with which polymers according to this invention can react. The use in nail varnish, make-ups and antiperspirants is also advantageous. As leather also displays free thiol groups because of cysteine partial structures in proteins, polymers of this invention are also useful for the impregnation of leather. An application of polymers of this invention in lacquers as well as in various cleaning agents and lubricants is also possible.

The invention includes the following embodiments:
(1) Polymeric compounds with thiol partial structures being present in form of disulfides with 2- and 6-mercapto(iso)nicotinamide.
(2) Polymeric compounds according to (1), wherein said polymeric compounds are mucoadhesive polymers adhering on porcine small intestinal mucosa in the rotating cylinder mucoadhesion test set up in form of test tablets (30 mg) with a diameter of 5 mm for more than 8 hours and in particular for more than 24 hours.
(3) Polymeric compounds according to (1) or (2), wherein said polymeric compounds are (crosslinked) poly(meth) acrylic acid, (trimethylated) chitosans, hyaluronic acid, pectins, alginates, methylcellulose, hydroxyethylcellulose or sodium carboxymethylcellulose.
(4) Polymeric compounds according to (1) to (3), wherein said polymeric compounds lead in combination with compounds exhibiting more than one thiol group to an increase in viscosity.
(5) Polymeric compounds according to (1) to (4), wherein thiolation of polymers described under claim 3 is achieved by the formation of amide bonds with cysteine, cysteamine, N-acetylcysteine, thioglycolic acid, mercaptobenzoic acid, mercaptonicotinic acid, glutathione or mercaptoaniline.
(6) Polymeric compounds according to (1) to (5), wherein said polymeric compounds display 10-1000 µmol of mercapto(iso)nicotinamide partial structures and in particular 100-1000 µmol of mercapto(iso)nicotinamide partial structures per gram polymer.
(7) Polymeric compounds according to (1) to (6), wherein said polymeric compounds are used as auxiliary agents in pharmaceutical, cosmetic and health-care products.
(8) Polymeric compounds according to (1) to (6), wherein said polymeric compounds are used for the impregnation of leather.

BRIEF DESCRIPTION OF THE DRAWINGS

Certain embodiments of the disclosure are described herein with reference to the accompanying figures in which.

EXAMPLES

Figure 1:
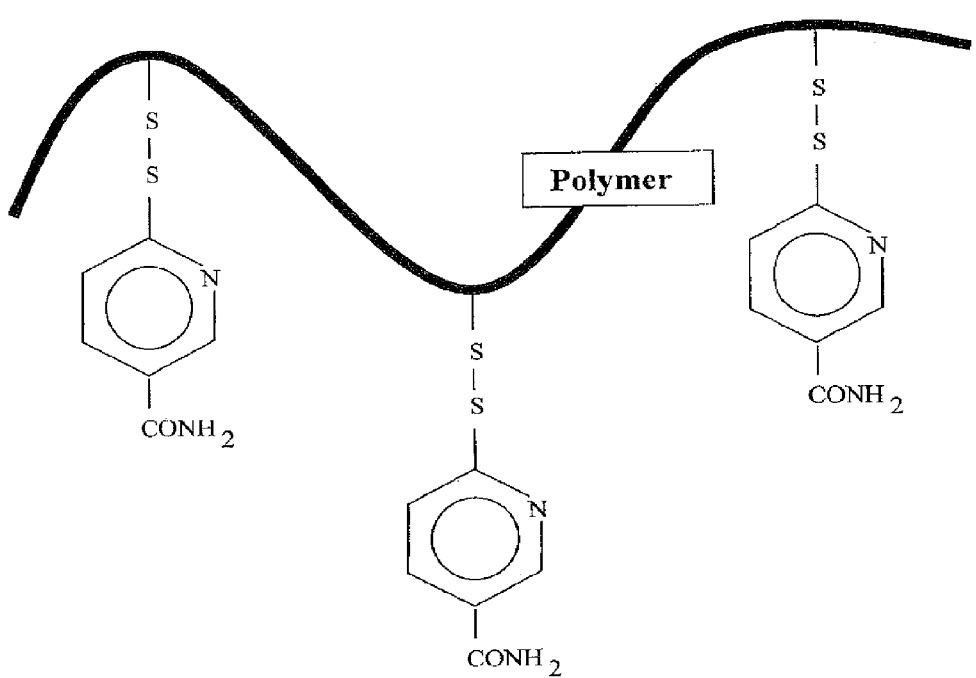
FIG. 1 illustrates vitamin B derivatives, in accordance with one or more embodiments of the disclosure.

The following examples shall illustrate the herein disclosed invention. Alterations and variations of the following examples can be made within the scope of the presented patent claims.

Example 1

Synthesis of 6-mercaptonicotinamide 5.0 g of 6-chloro-nicotinamide (31.9 mmol) and 2.65 g of thio urea (34.8 mmol) are suspended in absolute ethanol (50 ml) and heated under reflux (heating bath temperature: approximately 90° C.) for 6 hours. The reaction mixture becomes yellow over time. Thereafter, the reaction mixture is cooled down to room temperature. The resulting S-(5-carbamyl-2-pyridyl)thiuronium chloride is separated by filtration and brought to dryness. 6.7 g of the target compound (90%) are isolated in this way as yellow powder. $^1$H-NMR (200 MHz, DMSO-$d_6$, δ): 7.76 (br s, 1H); 7.83 (d, 1H, J=8.4 Hz); 8.33 (dd, 1H, J=8.4 Hz, J=2.0 Hz); 8.38 (br s, 1H); 9.05 (d, 1H, J=2.0 Hz); 9.69 (br s, 4H). 6.7 g of S-(5-carbamyl-2-pyridyl)thiuronium chloride (28.8 mmol) are suspended in water (30 ml) and 20 ml of 5 M NaOH are added. The suspension is stirred for 30 minutes at room temperature. Thereafter pH is adjusted to 4.9 by the addition of glacial acid. The raw product is isolated by filtration and recrystallised in an appropriate solvent (e.g. water) yielding 3.4 g of the target compound (69% based on 6-chloronicotinamide) in the form of a yellow powder. $^1$H-NMR (200 MHz, DMSO-$d_6$, δ): 7.29 (d, 1H, J=9.1 Hz); 7.46 (br s, 1H); 7.76 (dd, 1H, J=9.1 Hz, J=2.2 Hz); 7.95 (br s, 1H); 8.13 (d, 1H, J=2.2 Hz); 13.74 (br s, 1H).

Example 2

Synthesis of polyacrylic acid-cysteine-6-mercaptonicotinamide conjugates

One gram of polyacrylic acid 450 kDa (Sigma-Aldrich, Vienna) is hydrated in 200 ml of demineralised water and pH is adjusted to 5 by addition of 1 M NaOH. The carboxylic acid groups of the polymer are pre-activated at room temperature by the addition of 1-ethyl-3-(3-dimethylaminopropyl) carbodiimide hydrochloride in a final concentration of 200 mM under stirring for 30 minutes. After the addition of 1 g of cysteine pH is readjusted to 5 with HCl or NaOH if indicated and the reaction mixture is stirred for six hours at room temperature. The resulting polyacrylic acid-cysteine conjugate is dialysed against aqueous 1 mM hydrochloric acid solution, two times against the same dialysis medium but additionally containing 1% NaCl and finally exhaustively against water at 10° C. under light exclusion. Thereafter the pH of the conjugate is adjusted to 5 with 1 M NaOH. The isolated conjugate is lyophilized at −30° C. and stored at 4° C. The amount of covalently attached thiol groups is determined with Ellman's reagent.

The thiomer having been synthesized as described above exhibits 50-250 μmol of covalently attached thiol groups per gram polymer.

2.50 g of conjugate having been synthesized as described above (65 μmol—SH per gram of polymer) is dissolved in water (200 ml). The solution is brought to pH 6 with 1 M NaOH and 50 mg of 6-mercaptonicotinamide or 2-mercaptonicotinamide (dissolved in 5 ml of DMSO and 5 ml of water) as well as 20 mg of urea peroxide and 30 mg of maleic acid anhydride (both dissolved in 10 ml of water) are added. The solution is stirred at room temperature for 24 hours. Thereafter it is exhaustively dialysed against water and lyophilized.

Example 3

Synthesis of chitosan-thioglycolic acid-2- or -6-mercaptonicotinamide-conjugates One gram of chitosan is hydrated in 10 ml of 1 M HCl and in the following diluted with demineralized water in order to obtain a final concentration of 1% (m/v). 1 g of thioglycolic acid (TGA) and 1-ethyl-3-(3-dimethylaminopropyl) carbodiimide hydrochloride in a final concentration of 200 mM is added and the pH is readjusted to 5 with 1 M HCl or 1 M NaOH if needed. The reaction mixture is stirred at room temperature for six hours. The conjugate is dialysed against aqueous 1 mM hydrochloric acid solution, two times against the same dialysis medium but additionally containing 1% NaCl and finally exhaustively against water at 10° C. under light exclusion. Thereafter the pH of the conjugate is adjusted to 5. The isolated conjugate is lyophilized at −30° C. and stored at 4° C. The amount of covalently attached thiol groups is determined with Ellman's reagent.

2.50 g of chitosan-TGA (550 .mu.mol SH/g polymer) are dissolved in water (200 ml). The solution is adjusted to pH 6 with 1 M NaOH and 215 mg of 6-mercaptonicotinamide or 2-mercaptonicotinamide (dissolved in 5 ml of DMSO and 5 ml of water) and 130 mg of urea peroxide (dissolved in 10 ml of water) are added. The solution is stirred for 24 hours at room temperature. Thereafter the conjugate is exhaustively dialysed against demineralized water and lyophilized.

Example 4

Synthesis of pectin-4-aminothiophenol-2-mercaptonicotinamide-conjugates

One gram of pectin is dissolved in 250 ml of water/dioxane (2+1). After the continuous addition of 0.2 g of 4-mercaptoaniline dissolved in 3 ml of dioxane pH is adjusted to 4.5 with 0.5 M NaOH and 1-ethyl-3-(3-dimethylaminopropyl) carbodiimide hydrochloride is added in a final concentration of 200 mM. After three hours stirring at room temperature pH is adjusted to 7.5 and 0.2 g of sodium borhydride are added. The reaction mixture is stirred at 4° C. for one hour. Thereafter unbound 4-mercaptoaniline is removed by several extractions with ethylacetate. The resulting conjugate is precipitated by the addition of isopropyl alcohol and the precipitate is washed in pure isopropyl alcohol and acetone. The purified conjugate is dried in an exsiccator.

0.5 gram of pectin-4-aminothiophenol conjugate (420 μmol SH/g polymer) are hydrated in water (200 ml). The solution is adjusted to pH 6.5 with 1 M NaOH and 500 mg of 2-mercaptonicotinamide dissolved in 25 ml of DMSO and 25 ml of water are added. The solution is stirred for 24 hours at room temperature. Thereafter the conjugate is exhaustively dialysed against demineralized water and lyophilized.

Example 5

Mucoadhesion Test

Figure 2:
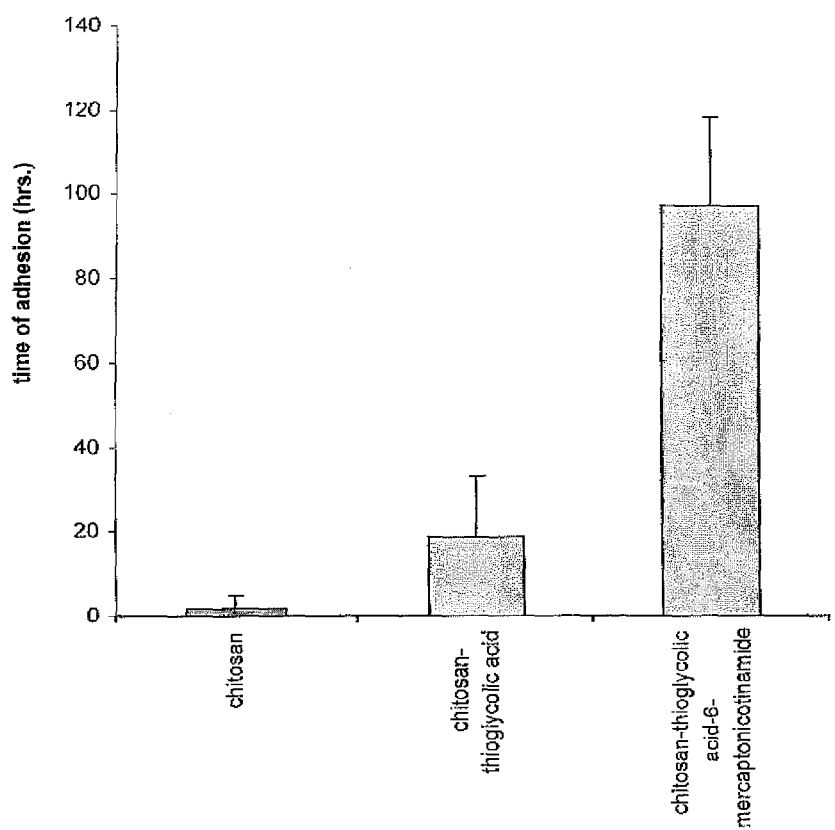
FIG. 2 depicts a graph of results of mucoadhesive testing, in accordance with one or more embodiments of the disclosure.

The mucoadhesive properties of polymers having been synthesized as described in Example 3 were determined according to a method described by Bernkop-Schnurch et al. [Bernkop-Schnurch et al., Int. J. Pharm., 260 (2003) 229-237]. Polymers with and without mercaptonicotinamide partial structures are compressed to tablets (30 mg) exhibiting a diameter of 5 mm. In the following they are attached with low pressure to freshly excised porcine small intestinal mucosa, which has been mounted on a steel cylinder. The cylinder is agitated with 100 rotations per minute in a dissolution test apparatus according to the European Pharmacopoeia having been filled with 50 mM phosphate buffer pH 6.5 at 37° C. The time point of detachment of tablets from the mucosa is visually determined. Results of this study are illustrated in FIG. 2 (means±standard deviation; n=4).

Example 6

Figure 3:
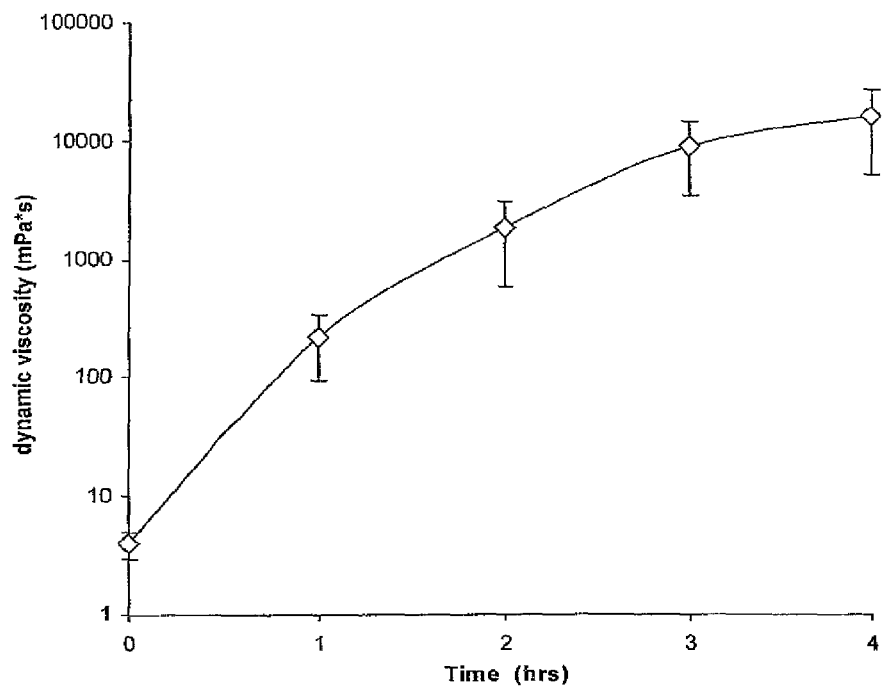
FIG. 3 depicts a graph of results of rheological studies, in accordance with one or more embodiments of the disclosure.

Rheological Studies 0.25 g of chitosan-thioglycolic acid-6-mercaptonicotinamide are hydrated in 50 ml of demineralized water. The resulting gel is added to 50 ml of 0.5% (m/v) chitosan-thioglycolic acid solution. The reaction mixture is homogenized and pH is adjusted to 6.0. At time points shown in FIG. 3 viscosity of the gel is measured (oscillating measurement at constant frequency of 1 Hz). Viscosity increases more than 1000-fold (means±standard deviation; n=4) within a few hours as illustrated in FIG. 3.

Example 7

Preparation of Tablets 20 g of polyacrylic acid-cysteine-6-mercaptonicotinamide (Example 2) are homogenized with 1 g of miconazole and directly compressed to tablets of 0.2 g of weight. These tablets show sufficiently high cohesive properties and a controlled release of the antimycotic drug.

Example 8

Preparation of Nose Drops 0.1 g of chitosan-thioglycolic acid-6-mercaptonicotinamide (Example 3) and 0.05 g of oxymetazoline HCl are dissolved in 100 ml of demineralised water and transferred to 10 ml dropper bottles. Optionally benzalkonium chloride in a final concentration of 0.015% (m/v) and EDTA in a final concentration of 0.05% (m/v) are added as preservatives.

Example 9

Preparation of A Hair Gel 0.25 g of chitosan-thioglycolic acid-6-mercaptonicotinamide (Example 3) and 0.25 g of chitosan-thioglycolic acid (Example 3) are hydrated in 100 ml of water/isopropyl alcohol (9+1). pH is adjusted to 6.0 with 1 M HCl or 1 M NaOH if needed. The resulting gel is filled in aliquots of 10 ml in sachets of aluminum/plastic composites. After opening of the sachets and the distribution on hair, viscosity of the gel increases strongly leading to a structure- and shape-providing effect.

The invention claimed is:

1. A polymeric compound comprising one of a 2-(iso)nicotinamide, a 6-(iso)nicotinamide and a 6-pyridoxine covalently bonded to a thiolated polymer.

2. The polymeric compound of claim 1, wherein the thiolated polymer comprises a (crosslinked) homo- or co-polymer consisting of (meth)acrylic acid, (meth)acrylic acid esters, (meth)acrylamides, vinylpyrrolidone, vinylalcohol, vinylimidazole, vinylcaprolactam, allylamine, (trimethylated) chitosans, hyaluronic acid, pectins, alginates, (crosslinked) polyallylamines, polylysine, polyornithine, polyaminoamides, methylcellulose, ethylcellulose, hydroxyethylcellulose, hydroxypropylmethylcellulose, and sodium carboxymethylcellulose, optionally exhibiting free thiol groups as side chains.

3. The polymeric compound of claim 2, wherein the one of a 2-(iso)nicotinamide, a 6-(iso)nicotinamide and a 6-pyridoxine is selected from the group consisting of S-(2- or 6-mercapto(iso)nicotinamide)- or S-(6-mercaptopyridoxine)-(homo)cysteine-disulfides, S-(2- or 6-mercapto(iso)nicotinamide)- or S-(6-mercaptopyridoxine)-cysteamine-disulfides, S-(2- or 6-mercapto(iso)nicotinamide)- or S-(6-mercaptopyridoxine)-N-acetlycysteine-disulfides, S-(2- or 6-mercapto(iso)nicotinamide)- or S-(6-mercaptopyridoxine)-thioglycolic acid-disulfides, S-(2- or 6-mercapto(iso)nicotinamide)- or S-(6-mercaptopyridoxine)-3-thiopropionic acid-disulfides, S-(2- or 6-mercapto(iso)nicotinamide)- or S-(6-mercaptopyridoxine)-4-thiobutanoic acid-disulfides, S-(2- or 6-mercapto(iso)nicotinamide)- or S-(6-mercaptopyridoxine)-mercaptobenzoic acid-disulfides, S-(2- or 6-mercapto(iso)nicotinamide)- or S-(6-mercaptopyridoxine)-mercaptonicotinic acid-disulfides, S-(2- or 6-mercapto(iso)nicotinamide)- or S-(6-mercaptopyridoxine)-glutathione-disulfides, S-(2- or 6-mercapto(iso)nicotinamide)- or S-(6-mercaptopyridoxine)-thioethylamidine-disulfides, S-(2- or 6-mercapto(iso)nicotinamide)- or S-(6-mercaptopyridoxine)-4-thiobutylamidine-disulfides, and S-(2- or 6-mercapto(iso)nicotinamide)- or S-(6-mercaptopyridoxine)-mercaptoaniline-disulfides, being attached to the polymer via amide, amidine or ester bonds.

4. The polymeric compound of claim 1, wherein 10-1000 μmol mercapto(iso)nicotinamide or mercaptopyridoxine-partial structures are present per gram of polymer.

5. The polymeric compound of claim 1, wherein 100 to 1000 μmol mercapto(iso)nicotinamide or mercaptopyridoxine-partial structures are present per gram of polymer.

6. The polymeric compound of claim 1, wherein said polymeric compound is a mucoadhesive polymer that adheres in a rotating cylinder mucoadhesion test system in a form of a test tablet of 30 mg weight and a diameter of 5 mm on porcine small intestinal mucosa for more than 8 hours.

7. The polymeric compound of claim 1, wherein a combination of the polymeric compound with compounds bearing more than one thiol group provides for an increase in viscosity.

8. A composition comprising at least one polymeric compound of claim 1, and further comprising at least one of a drug, an excipient, and a solvent.

* * * * *